United States Patent
Cesura et al.

(10) Patent No.: US 6,903,095 B2
(45) Date of Patent: Jun. 7, 2005

(54) PHTHALIMIDO DERIVATIVES AND A PROCESS FOR THEIR PREPARATION

(75) Inventors: Andrea Cesura, Crans-pres-Celigny (CH); Rosa Maria Rodriguez Sarmiento, Basel (CH); Andrew William Thomas, Birsfelden (CH); Rene Wyler, Zurich (CH)

(73) Assignee: Hoffmann-La Roche Inc., Nutley, NJ (US)

(*) Notice: Subject to any disclaimer, the term of this patent is extended or adjusted under 35 U.S.C. 154(b) by 64 days.

(21) Appl. No.: 10/657,857

(22) Filed: Sep. 9, 2003

(65) Prior Publication Data

US 2004/0229871 A1 Nov. 18, 2004

Related U.S. Application Data

(62) Division of application No. 10/387,950, filed on Mar. 13, 2003, now Pat. No. 6,660,736.

(30) Foreign Application Priority Data

Mar. 27, 2002 (EP) .............................................. 02007222

(51) Int. Cl.⁷ ..................... A61K 31/535; C07D 413/00
(52) U.S. Cl. .................. 514/233.5; 544/124; 546/277.1
(58) Field of Search .................. 514/233.5; 544/277.1; 546/124

(56) References Cited

U.S. PATENT DOCUMENTS

| 4,524,206 A | 6/1985 | New et al. |
| 5,304,556 A | 4/1994 | Yamamoto et al. |

FOREIGN PATENT DOCUMENTS

| EP | 504 574 | 9/1992 |
| WO | WO 96/40095 | 12/1996 |
| WO | WO 97/33572 | 9/1997 |
| WO | WO 01/34172 | 5/2001 |

OTHER PUBLICATIONS

Zhou et al., 253, pp. 169–174 (1997).
Schlaeger et al., Cytotechnology 30, pp. 71–83 (1999).

Primary Examiner—Joseph K. McKane
Assistant Examiner—Robin R. Waller
(74) Attorney, Agent, or Firm—George W. Johnston; Patricia S. Roca-Tramaloni; Kimberly J. Prior

(57) ABSTRACT

This invention relates to phthalimido derivatives of the formula

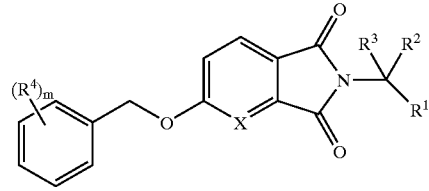

I wherein X is —N= or —CH=, and $R^1$ to $R^4$ and m are as defined in the specification, as well as their pharmaceutically acceptable salts. The invention further relates to pharmaceutical compositions containing these compounds, a method of treating a disease by administering a therapeutically effective amount of at least one of these compounds, and a process for their preparation for the treatment or prevention of diseases in which MAO-B inhibitors might be beneficial.

3 Claims, No Drawings

PHTHALIMIDO DERIVATIVES AND A PROCESS FOR THEIR PREPARATION

PRIORITY TO RELATED APPLICATIONS

This application is a Division of Ser. No. 10/387,950, filed Mar. 13, 2003 which is now U.S. Pat. No. 6,660,736.

FIELD OF THE INVENTION

This invention relates to phthalimido derivatives and a process for preparing these compounds.

BACKGROUND OF THE INVENTION

This invention relates to phthalimido derivatives of the formula

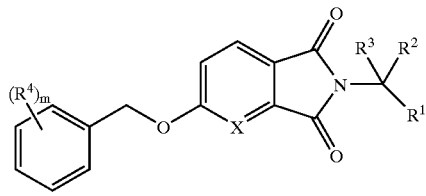

wherein
X is —N= or —CH=;
$R^1$ is —CO—$NR^5R^6$;
—$CHR^7$—$(CH_2)_n$—CO—$NR^5R^6$;
—$(CH_2)_n$—$NR^5R^6$;
—$(CH_2)_n$—$COOR^8$;
—$(CH_2)_n$—CN;
—$CHR^7$—$(CH_2)_n$—$CF_3$;
—$(CH_2)_n$—NH—$COR^9$;
—$(CH_2)_n$—NH—$COOR^8$;
—$(CH_2)_n$-piperidinyl, —$(CH_2)_n$-morpholinyl, —$(CH_2)_n$-tetrahydrofuranyl; —$(CH_2)_n$-thiophenyl or —$(CH_2)_n$-isoxazolyl, wherein the heterocyclic ring may be substituted by $C_1$–$C_6$-alkyl;
—$(CH_2)_n$-phenyl, wherein the phenyl ring may be substituted by halogen or halogen-($C_1$–$C_6$)-alkyl;
—$(CH_2)_p$—$OR^8$;
—$(CH_2)_p$—$SR^8$;
—$(CH_2)_p$—SO—$R^9$; or
—$(CH_2)_n$—CS—$NR^5R^6$;
$R^2$ is hydrogen;
$C_1$–$C_6$-alkyl;
—$(CH_2)_p$—$OR^{10}$;
—$(CH_2)_p$—$SR^{10}$; or benzyl;
$R^3$ is hydrogen or $C_1$–$C_6$-alkyl;
$R^4$ is halogen, halogen-($C_1$–$C_6$)-alkyl, cyano, $C_1$–$C_6$-alkoxy or halogen-($C_1$–$C_6$)-alkoxy;
$R^5$ and $R^6$ are independently from each other hydrogen or $C_1$–$C_6$-alkyl;
$R^7$ is hydrogen, hydroxy or $C_1$–$C_6$-alkoxy;
$R^8$ is hydrogen or $C_1$–$C_6$-alkyl;
$R^9$ is $C_1$–$C_6$-alkyl;
$R^{10}$ is hydrogen or $C_1$–$C_6$-alkyl;
m is 1, 2 or 3;
n is 0, 1 or 2; and
p is 1 or 2;
or a pharmaceutically acceptable salt thereof.

It has now been found that the compounds of formula I are selective monoamine oxidase B inhibitors.

Monoamine oxidase (MAO, EC 1.4.3.4) is a flavin-containing enzyme responsible for the oxidative deamination of endogenous monoamine neurotransmitters such as dopamine, serotonin, adrenaline, or noradrenaline, and trace amines, e.g. phenylethylamine, as well as a number of amine xenobiotics. The enzyme exists in two forms, MAO-A and MAO-B, encoded by different genes (A. W. Bach et al., Proc. Natl. Acad. Sci. USA 1988, 85, 4934–4938) and differing in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidised by both isoforms. MAO-B is widely distributed in several organs including brain (A. M. Cesura and A. Pletscher, Prog. Drug Research 1992, 38, 171–297). Brain MAO-B activity appears to increase with age. This increase has been attributed to the gliosis associated with aging (C. J. Fowler et al., J. Neural. Transm. 1980, 49, 1–20).

Additionally, MAO-B activity is significantly higher in the brains of patients with Alzheimer's disease (P. Dostert et al., Biochem. Pharmacol. 1989, 38, 555–561) and it has been found to be highly expressed in astrocytes around senile plaques (Saura et al., Neuroscience 1994, 70, 755–774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentué-Ferrer et al. in CNS Drugs 1996, 6, 217–236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., J. Clin. Psychiatry 1996, 57, 99–104), these adverse events are of less concern with reversible and selective MAO inhibitors, in particular of MAO-B. Thus, there is a need for MAO-B inhibitors with a high selectivity and without the adverse side-effects typical of irreversible MAO inhibitors with low selectivity for the enzyme.

SUMMARY OF THE INVENTION

This invention is directed to phthalimido derivatives of the formula

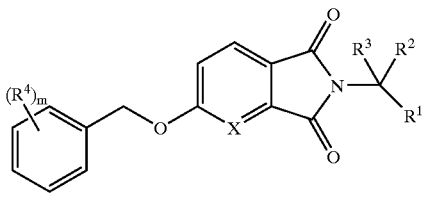

wherein
X is —N= or —CH=;
$R^1$ is —CO—NR$^5$R$^6$;
   —CHR$^7$—(CH$_2$)$_n$—CO—NR$^5$R$^6$;
   —(CH$_2$)$_n$—NR$^5$R$^6$;
   —(CH$_2$)$_n$—COOR$^8$;
   —(CH$_2$)$_n$—CN;
   —CHR$^7$—(CH$_2$)$_n$—CF$_3$;
   —(CH$_2$)$_n$—NH—COR$^9$;
   —(CH$_2$)$_n$—NH—COOR$^8$;
   —(CH$_2$)$_n$-piperidinyl, —(CH$_2$)$_n$-morpholinyl, —(CH$_2$)$_n$-tetrahydrofuranyl; —(CH$_2$)$_n$-thiophenyl or —(CH$_2$)$_n$-isoxazolyl, wherein the heterocyclic ring may be substituted by C$_1$–C$_6$-alkyl;
   —(CH$_2$)$_n$-phenyl, wherein the phenyl ring may be substituted by halogen or halogen-(C$_1$–C$_6$)-alkyl;
   —(CH$_2$)$_p$—OR$^8$;
   —(CH$_2$)$_p$—SR$^8$;
   —(CH$_2$)$_p$—SO—R$^9$; or
   —(CH$_2$)$_n$—CS—NR$^5$R$^6$;
$R^2$ is hydrogen;
   C$_1$–C$_6$-alkyl;
   —(CH$_2$)$_p$—OR$^{10}$;
   —(CH$_2$)$_p$—SR$^{10}$; or benzyl;
$R^3$ is hydrogen or C$_1$–C$_6$-alkyl;
$R^4$ is halogen, halogen-(C$_1$–C$_6$)-alkyl, cyano, C$_1$–C$_6$-alkoxy or halogen-(C$_1$–C$_6$)-alkoxy;
$R^5$ and $R^6$ are independently from each other hydrogen or C$_1$–C$_6$-alkyl;
$R^7$ is hydrogen, hydroxy or C$_1$–C$_6$-alkoxy;
$R^8$ is hydrogen or C$_1$–C$_6$-alkyl;
$R^9$ is C$_1$–C$_6$-alkyl;
$R^{10}$ is hydrogen or C$_1$–C$_6$-alkyl;
m is 1, 2 or 3;
n is 0, 1 or 2; and
p is 1 or 2;
or a pharmaceutically acceptable salt thereof.

The compounds of this invention have the advantageous properties mentioned above. It has been found that the compounds of formula I of the present invention and their pharmaceutically acceptable salts show the potential to be highly selective MAO-B inhibitors. Subjects of the present invention are further pharmaceutical compositions based on a compound of formula I in accordance with the invention, a method of treating a disease mediated by monoamine oxidase B inhibitors by administering a therapeutically effective amount of at least one of these compounds, and a process for preparing these compounds.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

The term "C$_1$–C$_6$-alkyl" ("lower alkyl") used in the present application denotes straight-chain or branched saturated hydrocarbon residues with 1 to 6 carbon atoms, preferably with 1 to 4 carbon atoms, such as methyl, ethyl, n-propyl, i-propyl, n-butyl, sec-butyl, t-butyl, and the like.

The term "halogen" denotes fluorine, chlorine, bromine and iodine.

"Halogen-(C$_1$–C$_6$)-alkyl" or "halogen-(C$_1$–C$_6$)-alkoxy" means the lower alkyl residue or lower alkoxy residue, respectively, as defined herein substituted in any position with one or more halogen atoms as defined herein. Examples of halogenalkyl residues include, but are not limited to, 1,2-difluoropropyl, 1,2-dichloropropyl, trifluoromethyl, 2,2,2-trifluoroethyl, 2,2,2-trichloroethyl, and 1,1,1-trifluoropropyl, and the like. "Halogenalkoxy" includes trifluoromethyloxy.

"C$_1$–C$_6$-Alkoxy" means the residue —O—R, wherein R is a lower alkyl residue as defined herein. Examples of alkoxy radicals include, but are not limited to, methoxy, ethoxy, isopropoxy, and the like.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid or base.

Such salts include:
(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, 2,2,2-trifluoroacetic acid, and the like; or
(2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) of the same acid addition salt.

Among compounds of the present invention certain compounds of formula I, or pharmaceutically acceptable salts thereof, are preferred.

Preferred compounds of formula I are those, in which X is —CH=.

Especially preferred are compounds of formula I, in which $R^1$ is —CO—NR$^5$R$^6$ or —CHR$^7$—(CH$_2$)$_n$—CO—NR$^5$R$^6$, and wherein $R^5$ and $R^6$ are independently from each other hydrogen or C$_1$–C$_6$-alkyl, $R^7$ is hydrogen, hydroxy or C$_1$–C$_6$-alkoxy and n is 0, 1 or 2.

Examples of such compounds are the following:
2-[5-(4-fluoro-benzyloxy)-1,3-dioxo-1,3-dihydro-isoindol-2-yl]-acetamide,
(S)-2-[5-(4-fluoro-benzyloxy)-1,3-dioxo-1,3-dihydro-isoindol-2-yl]-propionamide,
(S)-2-[5-(4-fluoro-benzyloxy)-1,3-dioxo-1,3-dihydro-isoindol-2-yl]-3-hydroxy-propionamide,
(R)-2-[5-(4-fluoro-benzyloxy)-1,3-dioxo-1,3-dihydro-isoindol-2-yl]-propionamide,
2-[5-(3-fluoro-benzyloxy)-1,3-dioxo-1,3-dihydro-isoindol-2-yl]-propionamide,
(2-[5-(3-fluoro-benzyloxy)-1,3-dioxo-1,3-dihydro-isoindol-2-yl]-acetamide, and
2-[5-(3-fluoro-benzyloxy)-1,3-dioxo-1,3-dihydro-isoindol-2-yl]-3-hydroxy-propionamide.

Also preferred are compounds of formula I, in which $R^1$ is —$(CH_2)_n$—$NR^5R^6$, —$(CH_2)_n$—NH—$COR^9$ or —$(CH_2)_n$-piperidinyl, and wherein $R^5$ and $R^6$ are independently from each other hydrogen or $C_1$–$C_6$-alkyl, $R^9$ is $C_1$–$C_6$-alkyl and n is 0, 1, or 2.

The following compounds are examples thereof:
N-{2-[5-(4-fluoro-benzyloxy)-1,3-dioxo-1,3-dihydro-isoindol-2-yl]-ethyl}-acetamide,
2-(2-amino-ethyl)-5-(4-fluoro-benzyloxy)-isoindole-1,3-dione, and
5-(4-fluoro-benzyloxy)-2-piperidin-4-yl-isoindole-1,3-dione.

Further preferred compounds of formula I are those, in which $R^1$ is —$(CH_2)_p$—$OR^8$ or —$CHR^7$—$(CH_2)_n$—$CF_3$, and wherein $R^7$ is hydrogen, hydroxy or $C_1$–$C_6$-alkoxy, $R^8$ is hydrogen or $C_1$–$C_6$-alkyl and p is 1 or 2. Examples of such compounds are the following:
5-(4-fluoro-benzyloxy)-2-(2-hydroxy-ethyl)-isoindole-1,3-dione,
5-(4-fluoro-benzyloxy)-2-(2-methoxy-ethyl)-isoindole-1,3-dione,
5-(3-fluoro-benzyloxy)-2-(2-methoxy-ethyl)-isoindole-1,3-dione,
(S)-5-(4-fluoro-benzyloxy)-2-(2-methoxy-1-methyl-ethyl)-isoindole-1,3-dione,
(S)-5-(3-fluoro-benzyloxy)-2-(2-methoxy-1-methyl-ethyl)-isoindole-1,3-dione,
(S)-5-(2-fluoro-benzyloxy)-2-(2-methoxy-1-methyl-ethyl)-isoindole-1,3-dione,
(S)-2-(2-methoxy-1-methyl-ethyl)-5-(4-trifluoromethyl-benzyloxy)-isoindole-1,3-dione,
(S)-5-(4-bromo-benzyloxy)-2-(2-methoxy-1-methyl-ethyl)-isoindole-1,3-dione,
(S)-5-(3,4-difluoro-benzyloxy)-2-(2-methoxy-1-methyl-ethyl)-isoindole-1,3-dione,
5-(3-fluoro-benzyloxy)-2-(2-hydroxy-ethyl)-isoindole-1,3-dione,
5-(4-fluoro-benzyloxy)-2-(3,3,3-trifluoro-2-hydroxy-propyl)-isoindole-1,3-dione, and
5-(3,5-bis-trifluoromethyl-benzyloxy)-2-(2-methoxy-1-methyl-ethyl)-isoindole-1,3-dione.

Preferred compounds of formula I are further those, in which $R^1$ is —$(CH_2)_p$—$SR^8$; —$(CH_2)_p$—SO—$R^9$; or —$(CH_2)_n$—CS—$NR^5R^6$, and wherein $R^5$ and $R^6$ are independently from each other hydrogen or $C_1$–$C_6$-alkyl, $R^8$ is hydrogen or $C_1$–$C_6$-alkyl, $R^9$ is $C_1$–$C_6$-alkyl and n is 0, 1, or 2. Examples of such are the following:
2-(2-ethylsulfanyl-ethyl)-5-(4-fluoro-benzyloxy)-isoindole-1,3-dione,
(S)-2-[5-(4-fluoro-benzyloxy)-1,3-dioxo-1,3-dihydro-isoindol-2-yl]-thiopropionamide, and
2-(2-ethylsulfanyl-ethyl)-5-(3-fluoro-benzyloxy)-isoindole-1,3-dione.

Also preferred are compounds of formula I, in which $R^1$ is —$(CH_2)_n$—CN and n is 0, 1 or 2. The following compounds are examples thereof:
5-(4-fluoro-benzyloxy)-1,3-dioxo-1,3-dihydro-isoindol-2-yl]-acetonitrile, and
[5-(3-fluoro-benzyloxy)-1,3-dioxo-1,3-dihydro-isoindol-2-yl]-acetonitrile.

Preferred are also compounds of formula I, in which $R^4$ signifies halogen. Especially preferred are compounds of formula I, in which $R^4$ is fluoro and m is 1.

The compounds of formula I and their pharmaceutically acceptable salts can be manufactured by reacting a compound of formula

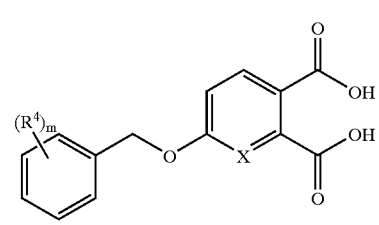

II with a compound of formula

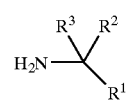

III to obtain a compound of formula

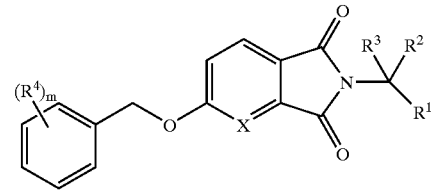

I and, if desired, converting a compound of formula I into a pharmaceutically acceptable salt.

Alternatively, the compounds of formula I and their pharmaceutically acceptable salts can be manufactured by reacting a compound of formula

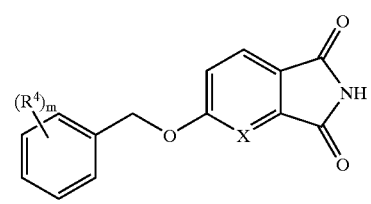

IV with a compound of formula

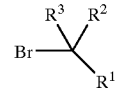

V to obtain a compound of formula

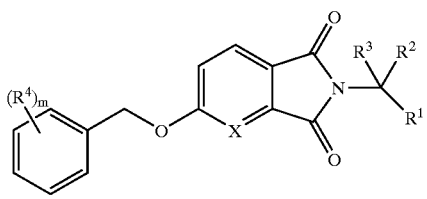

and, if desired, converting a compound of formula I into a pharmaceutically acceptable salt.

In accordance with the present invention, compounds of formula I can be prepared following scheme 1: A compound of formula VI is heated in the presence of ammonium carbonate. The obtained compound VII is then treated with benzylic bromides in the presence of potassium carbonate to afford compounds of type IV which are then dissolved in THF and treated with sodium hydride and an electrophile of formula V to give compounds of formula I.

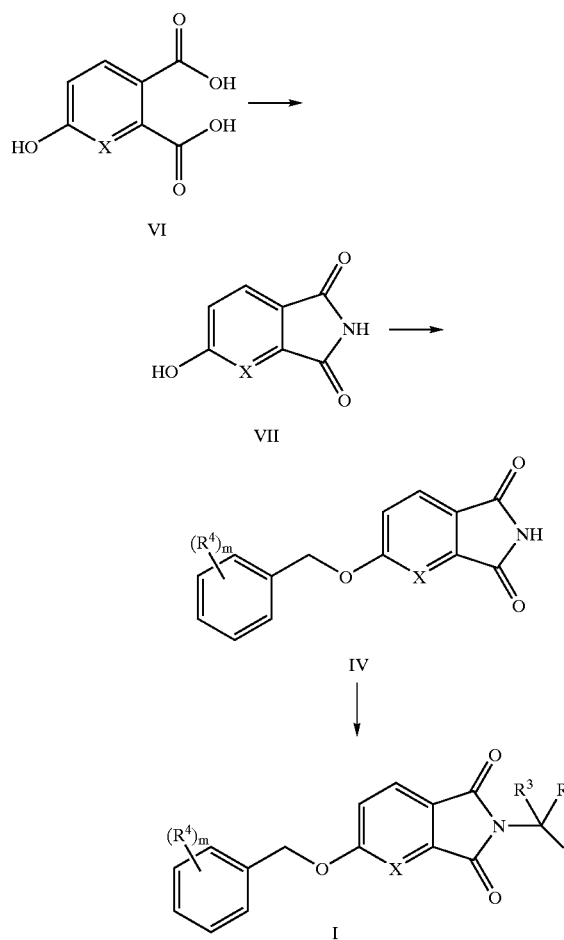

Alternatively, in accordance with the present invention, compounds of formula I can be prepared following scheme 2: A compound of formula VI is heated in the presence of benzylic bromides and potassium carbonate to afford VIII which are then saponified with bases such as LiOH to give IX. Treatment of IX with an activating agent such as carbonyldiimidazole in an appropriate solvent such as DMF or DMA or NMP, followed by heating (conventional or microwave) in the presence of amines III affords compounds of formula I.

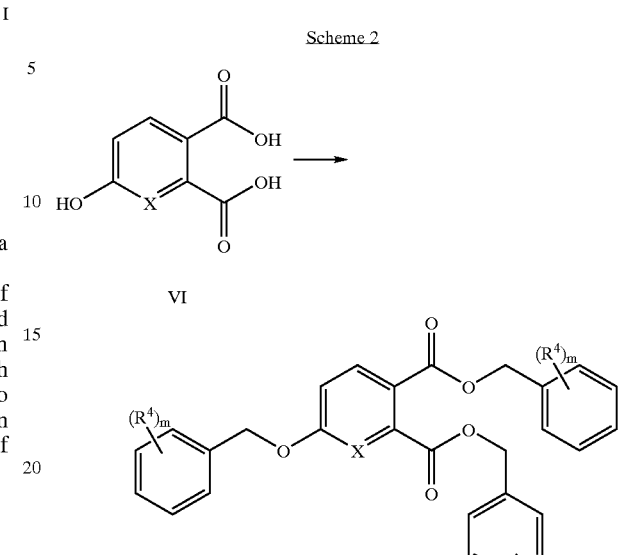

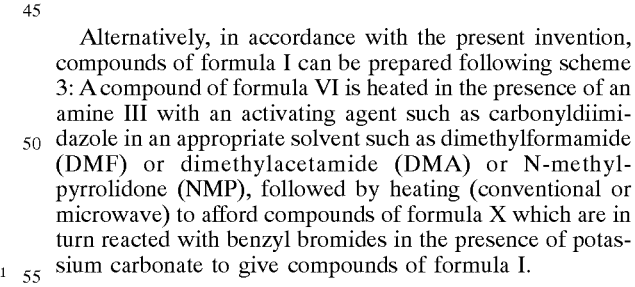

Alternatively, in accordance with the present invention, compounds of formula I can be prepared following scheme 3: A compound of formula VI is heated in the presence of an amine III with an activating agent such as carbonyldiimidazole in an appropriate solvent such as dimethylformamide (DMF) or dimethylacetamide (DMA) or N-methylpyrrolidone (NMP), followed by heating (conventional or microwave) to afford compounds of formula X which are in turn reacted with benzyl bromides in the presence of potassium carbonate to give compounds of formula I.

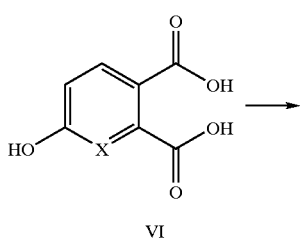

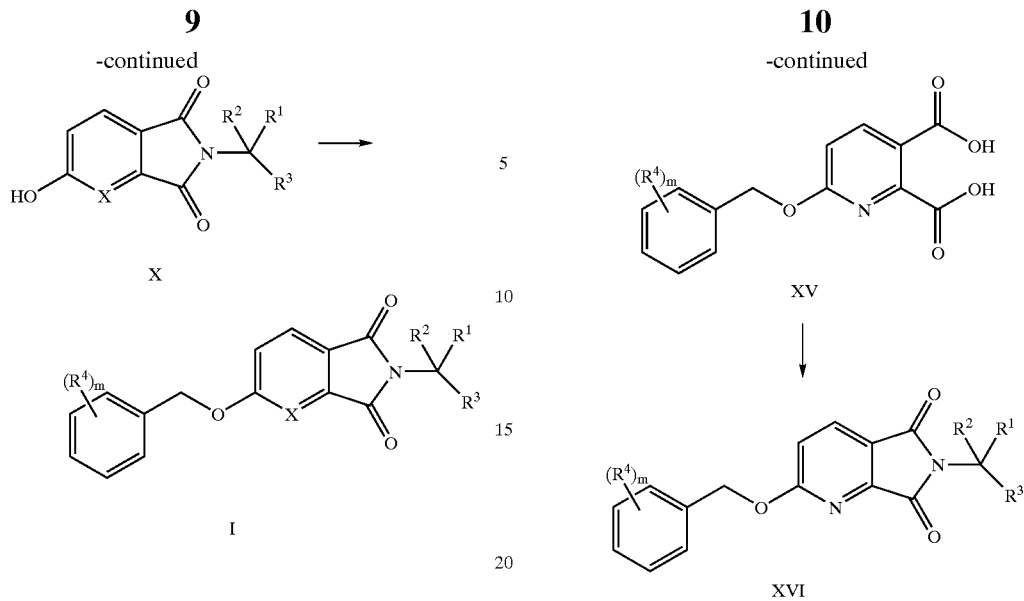

Alternatively, in accordance with the present invention, compounds of formula XVI can be prepared following scheme 4: A compound of formula XI is oxidized to XII and chlorinated to give XIII via successive treatment with m-chloroperoxybenzoic acid (m-CPBA) followed by phosphorus oxychloride. Subsequent reaction with sodium salts of benzyl alcohols affords XIV which after saponification to compounds of type XV are treated with an activating agent such as carbonyldiimidazole in an appropriate solvent such as DMF or DMA or NMP, followed by heating (conventional or microwave) in the presence of amines III affords compounds of formula XVI.

Scheme 4

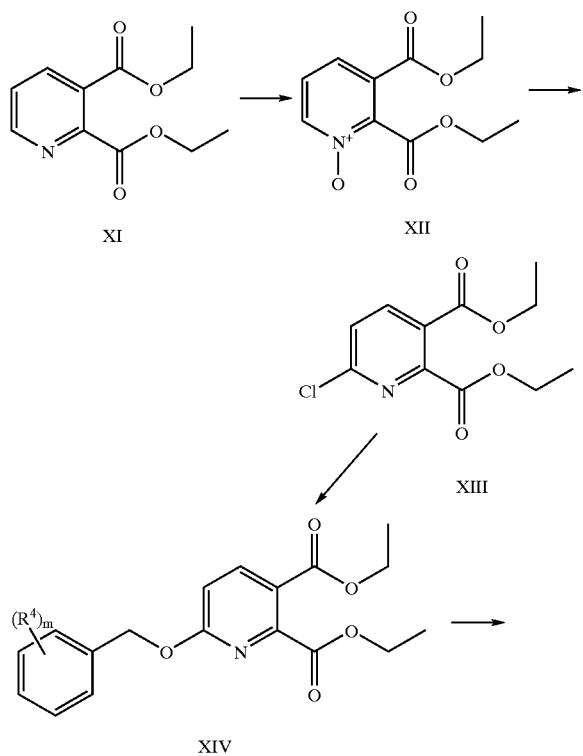

Pharmaceutically acceptable salts of compounds of formula I can be manufactured readily according to methods known in the art and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulfonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, monoamine oxidase B inhibitors and can be used for the treatment or prevention of diseases in which MAO-B inhibitors might be beneficial. These include acute and chronic neurological disorders, cognitive disorders and memory deficits. Treatable neurological disorders are for instance traumatic or chronic degenerative processes of the nervous system, such as Alzheimer's disease, other types of dementia, minimal cognitive impairment or Parkinson's disease. Other indications include psychiatric diseases such as depression, anxiety, panic attack, social phobia, schizophrenia, eating and metabolic disorders such as obesity as well as the prevention and treatment of withdrawal syndromes induced by abuse of alcohol, nicotine and other addictive drugs. Other treatable indications may be reward deficiency syndrome (G. M. Sullivan, International patent application No. WO 01/34172 A2), peripheral neuropathy caused by cancer chemotherapy (G. Bobotas, International Patent Application No. WO 97/33572 A1), or the treatment of multiple sclerosis (R. Y. Harris, International patent application No. WO 96/40095 A1) and other neuroinflammatory diseases.

The compounds of formula I and their pharmaceutically acceptable salts are especially useful for the treatment and prevention of Alzheimer's disease and senile dementia.

The pharmacological activity of the compounds was tested using the following method:

The cDNA's encoding human MAO-A and MAO-B were transiently transfected into EBNA cells using the procedure described by E.-J. Schlaeger and K. Christensen (Transient Gene Expression in Mammalian Cells Grown in Serum-free Suspension Culture; Cytotechnology, 15: 1–13, 1998). After transfection, cells were homogenized by means of a Polytron homogenizer in 20 mM Tris HCl buffer, pH 8.0, containing 0.5 mM EGTA and 0.5 mM phenylmethanesulfonyl fluoride. Cell membranes were obtained by centrifugation at 45,000×g and, after two rinsing step with 20 mM Tris HCl buffer, pH 8.0, containing 0.5 mM EGTA, membranes were eventually re-suspended in the above buffer and aliquots stored at −80° C. until use.

MAO-A and MAO-B enzymatic activity was assayed in 96-well-plates using a spectrophotometric assay adapted from the method described by M. Zhou and N. Panchuk-Voloshina (A One-Step Fluorometric Method for the Continuous Measurement of Monoamine Oxidase Activity, Analytical Biochemistry, 253: 169–174, 1997). Briefly, membrane aliquots were incubated in 0.1 M potassium phosphate buffer, pH 7.4, for 30 min at 37° C. with or without various concentrations of the compounds. After this period, the enzymatic reaction was started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples were further incubated for 30 min at 37° C. in a final volume of 200 μl and absorbance was then determined at a wavelength of 570 nm using a SpectraMax plate reader (Molecular Devices). Background (non-specific) absorbance was determined in the presence of 10 μM clorgyline for MAO-A or 10 μM L-deprenyl for MAO-B.

$IC_{50}$ values were determined from inhibition curves obtained using nine inhibitor concentrations in duplicate, by fitting data to a four parameter logistic equation using a computer program.

The compounds of the present invention are specific MAO-B inhibitors. The $IC_{50}$ values of compounds of formula I as measured in the assay described above are in the range of 10 μM or less, preferably of 1 μM or less, more preferably 0.03 μM or less, and most preferably 0.1 μM or less.

In the table below are described some specific $IC_{50}$ values of preferred compounds.

| Compound | $IC_{50}$ MAO-B (μM) | $IC_{50}$ MAO-A (μM) |
|---|---|---|
| (S)-2-[5-(4-Fluoro-benzyloxy)-1,3-dioxo-1,3-dihydro-isoindol-2-yl]-propionamide (Example 2) | 0.008 | 0.776 |
| 5-(4-Fluoro-benzyloxy)-1,3-dioxo-1,3-dihydro-isoindol-2-yl]-acetonitrile (Example 7) | 0.034 | >10 |
| 2-(2-Amino-ethyl)-5-(4-fluoro-benzyloxy)-isoindole-1,3-dione 1:1 hydrochloride (Example 9) | 0.032 | >10 |
| 5-(4-Fluoro-benzyloxy)-2-(2-hydroxy-ethyl)-isoindole-1,3-dione (Example 12) | 0.004 | 0.369 |
| (S)-2-[5-(4-Fluoro-benzyloxy)-1,3-dioxo-1,3-dihydro-isoindol-2-yl]-3-hydroxy-propionamide (Example 14) | 0.017 | >10 |
| 2-(2-Ethylsulfanyl-ethyl)-5-(4-fluoro-benzyloxy)-isoindole-1,3-dione (Example 19) | 0.011 | >10 |
| 4-[5-(4-Fluoro-benzyloxy)-1,3-dioxo-1,3-dihydro-isoindol-2-yl]-3-hydroxy-butyramide (Example 22) | 0.097 | >10 |
| (S)-5-(4-Bromo-benzyloxy)-2-(2-methoxy-1-methyl-ethyl)-isoindole-1,3-dione (Example 28) | 0.034 | >10 |
| (S)-5-(3-Methoxy-benzyloxy)-2-(2-methoxy-1-methyl-ethyl)-isoindole-1,3-dione (Example 29) | 0.069 | >10 |
| (S)-4-[2-(2-Methoxy-1-methyl-ethyl)-1,3-dioxo-2,3-dihydro-1H-isoindol-5-yloxymethyl]-benzonitrile (Example 30) | 0.129 | 6.200 |
| (S)-5-(3,4-Difluoro-benzyloxy)-2-(2-methoxy-1-methyl-ethyl)-isoindole-1,3-dione (Example 31) | 0.032 | 3.496 |
| (S)-2-(2-Methoxy-1-methyl-ethyl)-5-(4-trifluoromethoxy-benzyloxy)-isoindole-1,3-dione (Example 32) | 0.047 | >10 |
| 5-(4-Fluoro-benzyloxy)-2-thiophen-2-ylmethyl-isoindole-1,3-dione (Example 34) | 0.081 | >10 |
| 2-(2-Ethanesulfinyl-ethyl)-5-(4-fluoro-benzyloxy)-isoindole-1,3-dione (Example 38) | 0.115 | >10 |
| (5-(4-Fluoro-benzyloxy)-2-(3,3,3-trifluoro-2-methoxy-propyl)-isoindole-1,3-dione (Example 43) | 0.045 | >10 |
| (S)-2-[5-(3-Fluoro-benzyloxy)-1,3-dioxo-1,3-dihydro-isoindol-2-yl]-propionamide (Example 44) | 0.007 | 5.762 |
| 2-(2-Amino-ethyl)-5-(3-fluoro-benzyloxy)-isoindole-1,3-dione 1:1 hydrochloride (Example 50) | 0.039 | >10 |
| (S)-2-[5-(3-Fluoro-benzyloxy)-1,3-dioxo-1,3-dihydro-isoindol-2-yl]-3-hydroxy-propionamide (Example 52) | 0.020 | >10 |

The compounds of formula I and pharmaceutically acceptable salts thereof can be used in pharmaceutical compositions. The pharmaceutical compositions can be administered orally, e.g. in the form of tablets, coated tablets, dragrées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They may also contain other therapeutically valuable substances.

As mentioned earlier, this invention provides for pharmaceutical compositions containing a compound of formula I or pharmaceutically acceptable salts thereof and a therapeutically inert excipient, as is a process for the production of such pharmaceutical compositions, which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided for illustration of the invention. They should not be considered as limiting the scope of the invention, but merely as being representative thereof.

EXAMPLE 1

2-[5-(4-Fluoro-benzyloxy)-1,3-dioxo-1,3-dihydro-isoindol-2-yl]-acetamide a) 4-(4-Fluoro-benzyloxy)-phthalic acid bis-(4-fluoro-benzyl) ester A mixture of 4-hydroxyphthalic acid (3.5 g, 19 mmol), potassium carbonate (23.9 g, 173 mmol) and 4-fluorobenzylbromide (32.7 g, 173 mmol) in acetone (100 mL) and water (50 mL) was heated under reflux for 72 h. After cooling to room temperature, the mixture was evaporated and the product extracted with ethyl acetate. The organic extracts were then washed with brine, dried over sodium sulfate. Filtration and evaporation gave a residue which was purfied by chromatography ($SiO_2$, hexane-EtOAc 4:1) to afford the title compound (7.8 g, 80%) as a colorless oil.

MS: m/e=507.4 ($M+H^+$).

b) 4-(4-Fluoro-benzyloxy)-phthalic acid (Method A)

A mixture of 4-(4-fluoro-benzyloxy)-phthalic acid bis-(4-fluoro-benzyl) ester (7.8 g, 15.4 mmol) lithium hydroxide monohydrate (1.8 g, 46.2 mmol) in tetrahydrofuran (60 mL) and water (60 mL) was stirred at room temperature for 72 h. The mixture was then evaporated followed by acidification to pH 2 at 0° C. with concentrated HCl. The organic layer was then diluted with ethyl acetate, separared, washed with water and dried over sodium sulfate. Filtration and half evaporation gave a white suspension which was filtered off and washed with ether to afford the title compound (2.5 g, 56%) as a white solid.

MS: m/e=289.0 ($M-H^+$).

c) 4-(4-Fluoro-benzyloxy)-phthalic acid (Method B)

A mixture of 4-hydroxyphthalic acid (5.0 g, 27 mmol), potassium hydroxide (5.4 g, 30 mmol) and 4-fluorobenzylbromide (5.7 g, 30 mmol) in water (13 mL) was heated under reflux for 5 h. After cooling to room temperature, the mixture was washed with ether. The aqueous phase was then acidified to pH 2 at 0° C. with concentrated HCl and then extracted with ethyl acetate. The organic extracts were then washed with water and dried over sodium sulfate. Filtration and evaporation gave a residue which was purified by chromatography ($SiO_2$, $CHCl_3$:Acetone:AcOH:90:9:1) to afford the title compound (2.3 g, 29%) as a colorless oil. MS: m/e=289.0 ($M-H^+$).

d) 2-[5-(4-Fluoro-benzyloxy)-1,3-dioxo-1,3-dihydro-isoindol-2-yl]-acetamide

A mixture of 4-(4-fluoro-benzyloxy)-phthalic acid (185 mg, 0.64 mmol) and carbonyldiimidazole (109 mg, 0.67 mmol) in 1-methyl-2-pyrrolidinone (4 mL) was stirred at room temperature for 10 min and then heated at 50° C. for 15 min. To this mixture was added glycinamide hydrochloride (78 mg, 0.71 mmol) and pyridine (50 mg, 0.63 mmol) and the resulting mixture heated at 175 or 200° C. with microwave radiation (Smith reactor) for 10 min. After cooling to room temperature, the mixture was diluted with water and the resulting precipitate was filtered off and purified by chromatography ($SiO_2$, $CH_2Cl_2$: 2N NH3/MeOH 9:1) to afford the title compound (146 mg, 69%) as a white solid. MS: m/e=329.3. ($M+H^+$).

Alternatively, 2-[5-(4-fluoro-benzyloxy)-1,3-dioxo-1,3-dihydro-isoindol-2-yl]-acetamide was prepared from 5-hydroxy-isoindole-1,3-dione.

e) 5-Hydroxy-isoindole-1,3-dione

A mixture of 4-hydroxyphthalic acid (5.0 g, 27.0 mmol), acetic acid (25 mL), and ammonium carbonate (5.3 g, 55 mmol) was heated at 120° C. for 45 min followed by heating at 160° C. for 2 h. After cooling to room temperature, the reaction mixture was half-evaporated and then the reaction mixture was basified to pH 10 with 1 N NaOH followed by acidification to pH 5 at 0° C. with concentrated HCl. The resulting precipitate was filtered off, washed with water, dried at 60° C. under high vacuum over night, to afford the title compound (3.2 g, 71%) as an off-white crystalline solid.

MS: m/e=162.1 ($M-H^+$).

f) 5-(4-Fluoro-benzyloxy)-isoindole-1,3-dione

A mixture of 5-hydroxy-isoindole-1,3-dione (200 mg, 1.0 mmol), potassium carbonate (178 mg, 1.05 mmol), 4-fluorobenzylbromide (204 mg, 1.05 mmol) in ethanol (5 mL) was heated at 80° C. overnight. After cooling to room temperature, the reaction mixture was filtered and evaporated. The residue was purified by chromatography ($SiO_2$, heptane-$CH_2Cl_2$ 2:3 then $CH_2Cl_2$— 2N $NH_3$-MeOH 99:1: to 95:5) to afford the title compound (127 mg, 38%) as an off-white solid. MS: m/e=271.1 ($M^+$).

g) 2-[5-(4-Fluoro-benzyloxy)-1,3-dioxo-1,3-dihydro-isoindol-2-yl]-acetamide

A mixture of 5-(4-fluoro-benzyloxy)-isoindole-1,3-dione (100 mg, 0.37 mmol), sodium hydride (55% in mineral oil, 18 mg, 0.42 mmol) and 2-bromoacetamide (61 mg, 0.44 mmol) in dry tetrahydrofuran (5 mL) at 0° C. was stirred at room temperature for 3 h and then heated at 50° C. for 1 h. After cooling to 0° C., water (2 mL) was added and the product extracted with ethyl acetate. The organic extracts were then washed with brine and dried over sodium sulfate. Filtration and evaporation gave a residue which was purified by chromatography ($SiO_2$, heptane-$CH_2Cl_2$ 2:3 then $CH_2Cl_2$— 2N $NH_3$-MeOH 99:1: to 4:1) to afford the title compound (78 mg, 65%) as a white solid.

MS: m/e=329.3 ($M+H^+$).

EXAMPLE 2

(S)-2-[5-(4-Fluoro-benzyloxy)-1,3-dioxo-1,3-dihydro-isoindol-2-yl]-propionamide

As described for example 1d, 4-(4-fluoro-benzyloxy)-phthalic acid (185 mg, 0.64 mmol) was converted to the title compound (106 mg, 49%) (using H-alanine-$NH_2$ HCl instead of glycinamide hydrochloride) which was obtained as a white solid.

MS: m/e=343.3 ($M+H^+$).

EXAMPLE 3

(S)-2-[5-(4-Fluoro-benzyloxy)-1,3-dioxo-1,3-dihydro-isoindol-2-yl]-3-methyl-butyramide As described for example 1d, 4-(4-fluoro-benzyloxy)-phthalic acid (185 mg, 0.64 mmol) was converted to the title compound (115 mg, 48%) (using H-valine-NH$_2$ HCl instead of glycinamide hydrochloride) which was obtained as a white solid.

MS: m/e=371.3. (M+H$^+$).

EXAMPLE 4

(S)-2-[5-(4-Fluoro-benzyloxy)-1,3-dioxo-1,3-dihydro-isoindol-2-yl]-4-methyl-pentanoic acid amide As described for example 1d, 4-(4-fluoro-benzyloxy)-phthalic acid (185 mg, 0.64 mmol) was converted to the title compound (126 mg, 51%) (using H-leucine-NH$_2$ HCl instead of glycinamide hydrochloride) which was obtained as a white solid.

MS: m/e=385.3 (M+H$^+$).

EXAMPLE 5

(R,S)-[5-(4-Fluoro-benzyloxy)-1,3-dioxo-1,3-dihydro-isoindol-2-yl]-4-methylsulfanyl-butyramide As described for example 1d, 4-(4-fluoro-benzyloxy)-phthalic acid (165 mg, 0.57 mmol) was converted to the title compound (42 mg, 18%) (using DL-methionamide-HCl instead of glycinamide hydrochloride) which was obtained as an off-white foam.

MS: m/e=403.4 (M+H$^+$).

EXAMPLE 6

[5-(4-Fluoro-benzyloxy)-1,3-dioxo-1,3-dihydro-isoindol-2-yl]-acetic acid ethyl ester As described for example 1d, 4-(4-fluoro-benzyloxy)-phthalic acid (185 mg, 0.64 mmol) was converted to the title compound (110 mg, 48%) (using glycine ether ester-HCl instead of glycinamide hydrochloride) which was obtained as a white solid.

MS: m/e=358.2 (M+H$^+$).

EXAMPLE 7

5-(4-Fluoro-benzyloxy)-1,3-dioxo-1,3-dihydro-isoindol-2-yl]-acetonitrile

As described for example 1d, 4-(4-fluoro-benzyloxy)-phthalic acid (300 mg, 1.0 mmol) was converted to the title compound (215 mg, 67%) (using aminoacetonitrile instead of glycinamide hydrochloride) which was obtained as a white solid.

MS: m/e=328.2 (M+NH$_4^+$).

EXAMPLE 8

N-{2-[5-(4-Fluoro-benzyloxy)-1,3-dioxo-1,3-dihydro-isoindol-2-yl]-ethyl}-acetamide A mixture of 4-(4-fluoro-benzyloxy)-phthalic acid (185 mg, 0.64 mmol) and carbonyldiimidazole (109 mg, 0.67 mmol) in N,N-dimethylacetamide (3 mL) was stirred at room temperature for 10 min and then heated at 50° C. for 15 min. To this mixture was added N-acetylethylenediamine (78 mg, 0.76 mmol) and the resulting mixture heated under reflux for 20 min. After cooling to room temperature, the mixture was evaporated and the residue was purified by chromatography (SiO$_2$, CH$_2$Cl$_2$: 2N NH$_3$/MeOH 98:2 to 9:1) to afford the title compound (139 mg, 62%) as an off-white solid.

MS: m/e=357.3. (M+H$^+$).

EXAMPLE 9

2-(2-Amino-ethyl)-5-(4-fluoro-benzyloxy)-isoindole-1,3-dione 1:1 hydrochloride a) 2-[5-(4-Fluoro-benzyloxy)-1,3-dioxo-1,3-dihydro-isoindol-2-yl]-ethyl-carbamic acid tert-butyl ester As described for example 8, 4-(4-fluoro-benzyloxy)-phthalic acid (1.012 g, 3.5 mmol) was converted to the title compound (130 mg, 9%) [using tert-butyl N-(2-aminoethyl)-carbamate instead of N-acetylethylenediamine] which was obtained as a white solid.

MS: m/e=415.4 (M+H$^+$).

b) 2-(2-Amino-ethyl)-5-(4-fluoro-benzyloxy)-isoindole-1,3-dione 1:1 hydrochloride A mixture of {2-[5-(4-fluoro-benzyloxy)-1,3-dioxo-1,3-dihydro-isoindol-2-yl]-ethyl}-carbamic acid tert-butyl ester (200 mg, 0.5 mmol) and HCl in dioxane (4 N, 5 mL) was stirred at rt for 72 h. The precipitate was filtered off and washed with ether to afford the title compound (102 mg, 60%) as a white solid. MS: m/e=351.8 (M+H$^+$).

EXAMPLE 10

5-(4-Fluoro-benzyloxy)-2-(2-piperidin-1-yl-ethyl)-isoindole-1,3-dione

As described for example 8, 4-(4-fluoro-benzyloxy)-phthalic acid (200 mg, 0.7 mmol) was converted to the title compound (215 mg, 67%) [using 1-(2-aminoethyl)-piperidine instead of N-acetylethylenediamine] which was obtained as a light yellow solid.

MS: m/e=383.3 (M+H$^+$).

EXAMPLE 11

5-(4-Fluoro-benzyloxy)-2-(2-morpholin-4-yl-ethyl)-isoindole-1,3-dione

As described for example 8, 4-(4-fluoro-benzyloxy)-phthalic acid (200 mg, 0.7 mmol) was converted to the title compound (179 mg, 68%) [using 1-(aminoethyl)-morpholine instead of N-acetylethylenediamine] which was obtained as an off-white solid. MS: m/e=385.3 (M+H$^+$).

EXAMPLE 12

5-(4-Fluoro-benzyloxy)-2-(2-hydroxy-ethyl)-isoindole-1,3-dione

As described for example 8, 4-(4-fluoro-benzyloxy)-phthalic acid (200 mg, 0.7 mmol) was converted to the title compound (116 mg, 53%) [using ethanolamine instead of N-acetylethylenediamine] which was obtained as a white solid.

MS: m/e=316.2 (M+H$^+$).

EXAMPLE 13

5-(4-Fluoro-benzyloxy)-2-(2-methoxy-ethyl)-isoindole-1,3-dione

As described for example 8, 4-(4-fluoro-benzyloxy)-phthalic acid (200 mg, 0.7 mmol) was converted to the title compound (137 mg, 60%) [using 2-methoxyethylamine instead of N-acetylethylenediamine] which was obtained as a white solid.

MS: m/e=330.4 (M+H$^+$).

Alternatively, 5-(4-fluoro-benzyloxy)-2-(2-methoxy-ethyl)-isoindole-1,3-dione was also prepared starting from 5-hydroxy-2-(2-methoxy-ethyl)-isoindole-1,3-dione.

a) 5-Hydroxy-2-(2-methoxy-ethyl)-isoindole-1,3-dione

A mixture of 4-hydroxyphthalic acid (0.91 mg, 5.0 mmol) and carbonyldiimidazole (0.85 g, 5 mmol) in N,N-dimethylacetamide (3 mL) was stirred at room temperature for 45 min. To this mixture was added 2-methoxyethylamine (0.47 g, 6.0 mmol) and the resulting mixture heated under reflux for 15 min. After cooling to room temperature, the mixture was evaporated and the residue was purified by chromatography ($SiO_2$, $CH_2Cl_2$: 2N $NH_3$/MeOH 19:1 to 9:1) to afford the title compound (1.1 g, 95%) as a light yellow solid. MS: m/e=220.1 (M−H⁻).

b) 5-(4-Fluoro-benzyloxy)-2-(2-methoxy-ethyl)-isoindole-1,3-dione

A mixture of 5-hydroxy-2-(2-methoxy-ethyl)-isoindole-1,3-dione, from example 13a, (570 mg, 2.6 mmol), potassium carbonate (445 mg, 3.2 mmol) and 4-fluorobenzyl-bromide (526 mg, 2.8 mmol) in acetone (40 mL) was heated under reflux for 17 h. After cooling to room temperature, the mixture was filtered, evaporated and the residue was purified by crystallization from diethylether:heptane (1:2) to afford the title compound (560 mg, 66%) as a white solid. MS: m/e=330.4 (M+H⁺).

EXAMPLE 14

(S)-2-[5-(4-Fluoro-benzyloxy)-1,3-dioxo-1,3-dihydro-isoindol-2-yl]-3-hydroxy-propionamide As described for example 8, 4-(4-fluoro-benzyloxy)-phthalic acid (200 mg, 0.7 mmol) was converted to the title compound (126 mg, 51%) [using L-(−)-serinamide HCl and pyridine (65 mg, 0.8 mmol) instead of N-acetylethylenediamine] which was obtained as a white solid. MS: m/e=359.2 (M+H⁺).

EXAMPLE 15

(S)-2-[5-(4-Fluoro-benzyloxy)-1,3-dioxo-1,3-dihydro-isoindol-2-yl]-propionic acid methyl ester As described for example 14, 4-(4-fluoro-benzyloxy)-phthalic acid (200 mg, 0.7 mmol) was converted to the title compound (148 mg, 53%) [using L-alanine methyl ester-HCl instead of L-(−)-serinamide HCl] which was obtained as a white solid after crystallization from MeOH. MS: m/e=358.2 (M+H⁺).

EXAMPLE 16

(S)-2-[5-(4-Fluoro-benzyloxy)-1,3-dioxo-1,3-dihydro-isoindol-2-yl]-3-phenyl-propionamide As described for example 8, 4-(4-fluoro-benzyloxy)-phthalic acid (200 mg, 0.7 mmol) was converted to the title compound (221 mg, 77%) [using L-(−)-phenylalanine-amide instead of N-acetylethylenediamine] which was obtained as a white solid.

MS: m/e=359.2 (M+H⁺).

EXAMPLE 17

(R)-2-[5-(4-Fluoro-benzyloxy)-1,3-dioxo-1,3-dihydro-isoindol-2-yl]-propionamide As described for example 14, 4-(4-fluoro-benzyloxy)-phthalic acid (200 mg, 0.7 mmol) was converted to the title compound (148 mg, 53%) [using H-D-Ala-$NH_2$ HCl instead of L-(−)-serinamide HCl] which was obtained as a white solid after trituration with MeOH. MS: m/e=343.2 (M+H⁺).

EXAMPLE 18

2-[5-(4-Fluoro-benzyloxy)-1,3-dioxo-1,3-dihydro-isoindol-2-yl]-3-phenyl-propionamide As described for example 8, 4-(4-fluoro-benzyloxy)-phthalic acid (1.2 g, 4.0 mmol) was converted to the title compound (200 mg, 13%) [using 2-methylalanine methyl ester instead of N-acetylethylenediamine] which was obtained as a white solid.

MS: m/e=372.3 (M+H⁺).

EXAMPLE 19

2-(2-Ethylsulfanyl-ethyl)-5-(4-fluoro-benzyloxy)-isoindole-1,3-dione

As described for example 8, 4-(4-fluoro-benzyloxy)-phthalic acid (290 mg, 1.0 mmol) was converted to the title compound (212 mg, 59%) [2-(ethylthio)ethylamine instead of N-acetylethylenediamine] which was obtained as a white solid after crystallization from MeOH. MS: m/e=360.2 (M+H⁺).

EXAMPLE 20

(R,S)-2-[5-(4-Fluoro-benzyloxy)-1,3-dioxo-1,3-dihydro-isoindol-2-yl]-butyramide As described for example 1c, 4-(4-fluoro-benzyloxy)-phthalic acid (290 mg, 1.0 mmol) was converted to the title compound (210 mg, 59%) [using (rac)-2-aminobutyramide hydrochloride instead of glycinamide hydrochloride and N,N-dimethylacetamide instead of 1-methyl-2-pyrrolidinone] which was obtained as a white solid. MS: m/e=357.3 (M+H⁺).

EXAMPLE 21

4-[5-(4-Fluoro-benzyloxy)-1,3-dioxo-1,3-dihydro-isoindol-2-yl]-butyramide

As described for example 20, 4-(4-fluoro-benzyloxy)-phthalic acid (290 mg, 1.0 mmol) was converted to the title compound (103 mg, 29%) [using 4-aminobutyramide hydrochloride instead of (rac)-2-aminobutyramide hydrochloride] which was obtained as a white solid after crystallization from MeOH. MS: m/e=357.3 (M+H⁺).

EXAMPLE 22

4-[5-(4-Fluoro-benzyloxy)-1,3-dioxo-1,3-dihydro-isoindol-2-yl]-3-hydroxy-butyramide As described for example 21, 4-(4-fluoro-benzyloxy)-phthalic acid (290 mg, 1.0 mmol) was converted to the title compound (108 mg, 22%) [using 4-amino-3-hydroxybutyramide hydrochloride instead of 4-aminobutyramide hydrochloride] which was obtained as an off-white solid. MS: m/e=373.3 (M+H⁺).

EXAMPLE 23

5-(3-Fluoro-benzyloxy)-2-(2-methoxy-ethyl)-isoindole-1,3-dione

As described for example 13b, a mixture of 5-hydroxy-2-(2-methoxy-ethyl)-isoindole-1,3-dione (example 13a, 400 mg, 1.8 mmol) was converted to title compound (427 mg, 72%) (using 3-fluorobenzylbromide instead of 4-fluorobenzylbromide) (376 mg, 2.0 mmol) and heating under reflux for 67 h which was obtained as a white solid after purification by chromatography ($SiO_2$, $CH_2Cl_2$: 2N $NH_3$/MeOH 99:1 to 19:1).

MS: m/e=330.4 (M+H⁺).

EXAMPLE 24

(S)-5-(4-Fluoro-benzyloxy)-2-(2-methoxy-1-methyl-ethyl)-isoindole-1,3-dione As described for example 8, 4-(4-fluoro-benzyloxy)-phthalic acid (300 mg, 1.0 mmol) was converted to the title compound (286 mg, 81%) [using (S)-1-methoxy-2-propylamine instead of N-acetylethylenediamine] which was obtained as a white solid after trituration with hexane. MS: m/e=344.4 (M+H$^+$).

EXAMPLE 25

(S)-5-(3-Fluoro-benzyloxy)-2-(2-methoxy-1-methyl-ethyl)-isoindole-1,3-dione a) (S)-5-Hydroxy-2-(2-methoxy-1-methyl-ethyl)-isoindole-1,3-dione As described for example 13a, 4-hydroxyphthalic acid (8.0 g, 44 mmol) was converted to the title compound (8.7 g, 84%) [using (S)-1-methoxy-2-propylamine instead of 2-methoxyethylamine] which was obtained as light-yellow crystals after purification by chromatography (SiO$_2$, EtOAc:Hexane 1:1). MS: m/e=234.1 (M−H$^-$).

b) (S)-5-(3-Fluoro-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (example 25a, 200 mg, 0.9 mmol) was converted to title compound (200 mg, 69%) %) (using 3-fluorobenzylbromide instead of 4-fluorobenzyl-bromide), after heating under reflux for 1 h, which was obtained as a white solid after crystallization from ethylacetate:hexane (1:1). MS: m/e=343.2 (M$^+$).

EXAMPLE 26

(S)-5-(2-Fluoro-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (example 25a, 200 mg, 0.9 mmol) was converted to the title compound (235 mg, 81%) (using 2-fluorobenzylbromide instead of 4-fluorobenzyl-bromide), after heating under reflux for 1 h, which was obtained as a white solid after crystallization from ethylacetate:hexane (1:1). MS: m/e=343.2 (M$^+$).

EXAMPLE 27

(S)-2-(2-Methoxy-1-methyl-ethyl)-5-(4-trifluoromethyl-benzyloxy)-isoindole-1,3-dione As described for example 23, a mixture of (S)-5-hydroxy-2-(2-methoxy-1-methyl-ethyl)-isoindole-1,3-dione (example 25a, 200 mg, 0.9 mmol) was converted to the title compound (265 mg, 79%) [using 4-(trifluoromethyl)benzylbromide instead of 4-fluorobenzylbromide], after heating under reflux for 1.5 h, which was obtained as a white solid after crystallization from ethylacetate:hexane (1:1). MS: m/e=393.2 (M$^+$).

EXAMPLE 28

(S)-5-(4-Bromo-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (example 25a, 200 mg, 0.9 mmol) was converted to the title compound (296 mg, 86%) (using 4-bromobenzylbromide instead of 4-fluorobenzylbromide), after heating under reflux for 1.5 h, which was obtained as a white solid after crystallization from ethylacetate:hexane (1:1). MS: m/e=403.2/405.2 (M$^+$).

EXAMPLE 29

(S)-5-(3-Methoxy-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (example 25a, 200 mg, 0.9 mmol) was converted to the title compound (280 mg, 93%) (using 3-methoxybenzylbromide instead of 4-fluorobenzylbromide), after heating under reflux for 3 h, which was obtained as a white solid after crystallization from ethylacetate:hexane (1:1). MS: m/e=355.4 (M$^+$).

EXAMPLE 30

(S)-4-[2-(2-Methoxy-1-methyl-ethyl)-1,3-dioxo-2,3-dihydro-1H-isoindol-5-yloxymethyl]-bezonitrile As described for example 23, a mixture of (S)-5-hydroxy-2-(2-methoxy-1-methyl-ethyl)-isoindole-1,3-dione (example 25a, 200 mg, 0.9 mmol) was converted to the title compound (280 mg, 94%) (using 3-bromomethyl benzonitrile instead of 4-fluorobenzyl-bromide), after heating under reflux for 1.5 h, which was obtained as a white solid after crystallization from ethylacetate:hexane (1:1). MS: m/e=350.2 (M$^+$).

EXAMPLE 31

(S)-5-(3,4-Difluoro-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (example 25a, 200 mg, 0.9 mmol) was converted to title compound (235 mg, 77%) (using alpha-bromo-3,4-difluorotoluene instead of 4-fluorobenzylbromide), after heating under reflux for 2 h, which was obtained as a white solid after crystallization from ethylacetate:hexane (1:1). MS: m/e=361.2 (MH).

EXAMPLE 32

(S)-2-(2-Methoxy-1-methyl-ethyl)-5-(4-trifluoromethoxy-benzyloxy)-isoindole-1,3-dione As described for example 23, a mixture of (S)-5-hydroxy-2-(2-methoxy-1-methyl-ethyl)-isoindole-1,3-dione (example 25a, 200 mg, 0.9 mmol) was converted to the title compound (306 mg, 88%) [using (4-trifluoromethoxy)benzyl bromide instead of 4-fluorobenzylbromide], after heating under reflux for 3 h, which was obtained as a white solid after crystallization from ethylacetate:hexane (1:1). MS: m/e=409.4 (M+H$^+$).

EXAMPLE 33

5-(4-Fluoro-benzyloxy)-2-(tetrahydro-furan-2-ylmethyl)-isoindole-1,3-dione

As described for example 1d, 4-(4-fluoro-benzyloxy)-phthalic acid (290 mg, 1.0 mmol) was converted to the title compound (249 mg, 70%) [using tetrahydrofurfurylamine instead of glycinamide hydrochloride and pyridine; and N,N-dimethylacetamide instead of 1-methyl-2-pyrrolidinone] which was obtained as a white solid.
MS: m/e=356.3 (M+H$^+$).

EXAMPLE 34

5-(4-Fluoro-benzyloxy)-2-thiophen-2-ylmethyl-isoindole-1,3-dione

As described for example 33, 4-(4-fluoro-benzyloxy)-phthalic acid (290 mg, 1.0 mmol) was converted to the title compound (269 mg, 73%) [using 2-thiophenemethylamine instead of tetrahydrofurfurylamine] which was obtained as a white solid.

MS: m/e=367.1 (M+H$^+$).

EXAMPLE 35

(S)-2-[5-(4-Fluoro-benzyloxy)-1,3-dioxo-1,3-dihydro-isoindol-2-yl]-thiopropionamide A mixture of (S)-2-[5-(4-fluoro-benzyloxy)-1,3-dioxo-1,3-dihydro-isoindol-2-yl]-propionamide (171 mg, 0.5 mmol) and Lawesson's reagent (243 mg, 0.6 mmol) in tetrahydrofuran (20 mL) was stirrred at room temperature for 72 h. Then the mixture was evaporated and the residue was purified by chromatography (SiO$_2$, CH$_2$Cl$_2$: 2N NH$_3$/MeOH 99:1 to 19:1) to afford the title compound (65 mg, 36%) as an off-white solid after recrystallisation from MeOH. MS: m/e=359.2 (M+H$^+$).

EXAMPLE 36

5-(4-Fluoro-benzyloxy)-2-piperidin-4-yl-isoindole-1, 3-dione 1:1 hydrochloride

As described for example 33, 4-(4-fluoro-benzyloxy)-phthalic acid (590 mg, 2.0 mmol) was converted to the title compound [using using 4-amino-1-Boc-piperidine instead of tetrahydrofurfurylamine] followed by treatment with HCl in dioxane (4 N, 2 mL) and stirring at room temperature for 12 h. The precipitate was filtered off and washed with acetone and ether to afford the title compound (73 mg, 9%) as a white solid.

MS: m/e=355.3 (M+H$^+$).

EXAMPLE 37

5-(4-Fluoro-benzyloxy)-2-(5-methyl-isoxazol-3-yl)-isoindole-1,3-dione

As described for example 33, 4-(4-fluoro-benzyloxy)-phthalic acid (290 mg, 1.0 mmol) was converted to the title compound (166 mg, 47%) [using 3-amino-5-methylisoxazole instead of tetrahydrofurfurylamine] as a white solid.

MS: m/e=353.3 (M+H$^+$).

EXAMPLE 38

2-(2-Ethanesulfinyl-ethyl)-5-(4-fluoro-benzyloxy)-isoindole-1,3-dione

A mixture of 2-(2-ethylsulfanyl-ethyl)-5-(4-fluoro-benzyloxy)-isoindole-1,3-dione (96 mg, 0.27 mmol) and 3-phenyl-2-(phenylsulfonyl)oxaziridine (84 mg, 0.32 mmol) in CH$_2$Cl$_2$ (3 mL) was stirred at room temperature for 72 h. Then the mixture was evaporated and the residue was purified by chromatography (SiO$_2$, CH$_2$Cl$_2$: 2N NH$_3$/MeOH 97:3 to 9:1) to afford the title compound (34 mg, 34%) as a white solid.

MS: m/e=375.2 (M+H$^+$).

EXAMPLE 39

(S)-2-[2-(4-Fluoro-benzyloxy)-5,7-dioxo-5,7-dihydro-pyrrolo[3,4-b]pyridin-6-yl]-propionamide
a) 1-Oxy-pyridine-2,3-dicarboxylic acid diethyl ester A mixture of diethyl 2,3-pyridinedicarboxylate (10 g, 45 mmol) and 3-chloroperoxy-benzoic acid (13.8 g, 56 mmol) in CH$_2$Cl$_2$ (150 mL) was stirred at 0° C. and allowed to warm up room temperature over 30 min and left overnight. Then half-evaporation gave a residue which was purified by chromatography (SiO$_2$, EtOAc:EtOAc:MeOH, 19:1) to afford the title compound (8.2 g, 77%) as a white solid. MS: m/e=239.2 (M$^+$)
b) 6-Chloro-pyridine-2,3-dicarboxylic acid diethyl ester A mixture of 1-oxy-pyridine-2,3-dicarboxylic acid diethyl ester (8.0 g, 33 mmol) and phosphoryloxychloride (25.6 g, 167 mmol) was heated at 100° C. for 1.5 h. After cooling to room temperature, the mixture was evaporated and then diluted with CH$_2$Cl$_2$. Then the organic phase was washed with water, brine and then dried over sodium sulfate. Filtration and evaporation gave a residue which was purified by chromatography (SiO$_2$, heptane-EtOAc 9:1 to 1:1) to afford the title compound (5.5 g, 63%) as a colorless oil.

MS: m/e=258.1 (M+H$^+$).
c) 6-(4-Fluoro-benzyloxy)-pyridine-2,3-dicarboxylic acid diethyl ester A mixture of sodium hydride (55% in mineral oil, 254 mg, 0.6 mmol) and 4-fluorobenzylalcohol in tetrahydrofuran (30 mL) was heated at 60° C. for 30 min and then after cooling at 0° C. a solution of 6-chloro-pyridine-2,3-dicarboxylic acid diethyl ester (1.3 g. 0.5 mmol) in tetrahydrofuran (20 mL) was added over 10 min. The resulting mixture was kept at 0° C. for 1 h and then water was added. The mixture was then extracted with ethylacetate and the combined organic extracts washed with water, brine and then dried over sodium sulfate. Filtration and evaporation gave a residue which was purified by chromatography (SiO$_2$, heptane-EtOAc 9:1 to 3:1) to afford the title compound (1.3 g, 74%) as a colorless oil. MS: m/e=348.4 (M+H$^+$).
d) 6-(4-Fluoro-benzyloxy)-pyridine-2,3-dicarboxylic acid diethyl ester A mixture of 6-(4-fluoro-benzyloxy)-pyridine-2,3-dicarboxylic acid diethyl ester (1.2 g, 3.5 mmol) and potassium hydroxide (0.6 g, 11.5 mmol) in water (25 mL) and tetrahydrofuran (10 mL) was heated at 80° C. for 4 h. After cooling to room temperature, the mixture was washed with ether. The aqueous phase was then acidified to pH 2 at 0° C. with concentrated HCl and then extracted with ethyl acetate. The organic extracts were then washed with water and brine and dried over sodium sulfate. Filtration and evaporation gave a residue which was purified by crystallization from diethylether:heptane (2:1) to afford the title compound (0.9 g, 88%) as a white solid.

MS: m/e=290.0 (M−H$^−$).
e) (S)-2-[2-(4-Fluoro-benzyloxy)-5,7-dioxo-5,7-dihydro-pyrrolo[3,4-b]pyridin-6-yl]-propionamide As described for example 14, 4-(4-fluoro-benzyloxy)-phthalic acid (200 mg, 0.7 mmol) was converted to the title compound (40 mg, 12%) [using H-Ala-NH$_2$ HCl instead of L-(−)-serinamide HCl] which was obtained as a white solid after purification by HPLC (Waters Xterra RP18 (5 μm×50× 19 mm) eluting with AcCN/0.1%TFA/Water.

MS: m/e=344.3 (M+H$^+$).

EXAMPLE 40

5-(4-Fluoro-benzyloxy)-2-(3-morpholin-4-yl-propyl)-isoindole-1,3-dione
a) 5-Hydroxy-2-(3-morpholin-4-yl-propyl)-isoindole-1,3-dione As described for example 13a, 4-hydroxyphthalic acid (1.0 g, 5.5 mmol) was converted to the title compound (780 mg, 49%) [using 4-(3-aminopropyl)morpholine instead of 2-methoxyethylamine] which was obtained as a light yellow solid.

MS: m/e=291.3 (M+H$^+$).

b) 5-(4-Fluoro-benzyloxy)-2-(3-morpholin-4-yl-propyl)-isoindole-1,3-dione

As described for example 13b, 5-hydroxy-2-(3-morpholin-4-yl-propyl)-isoindole-1,3-dione (770 mg, 2.65 mmol) was converted to the title compound (210 mg, 28%) which was obtained as a white solid after purification by chromatography (SiO$_2$, CH$_2$Cl$_2$: 2N NH$_3$/MeOH 99:1 to 19:1). MS: m/e=399.4 (M+H$^+$).

EXAMPLE 41

2-(4-Fluoro-benzyl)-5-(4-fluoro-benzyloxy)-isoindole-1,3-dione

A mixture of 5-hydroxy-isoindole-1,3-dione (200 mg, 1.0 mmol), potassium carbonate (178 mg, 1.05 mmol), 4-fluorobenzylbromide (204 mg, 1.05 mmol) in ethanol (5 mL) was heated at 80° C. overnight. After cooling to room temperature, the reaction mixture was filtered and evaporated. The residue was purified by chromatography (SiO$_2$, heptane-CH$_2$Cl$_2$ 2:3 then CH$_2$Cl$_2$— 2N NH$_3$-MeOH 99:1 to 95:5) to afford the title compound (13 mg, 3%) as a white solid. MS: m/e=379.4 (M$^+$).

EXAMPLE 42

5-(4-Fluoro-benzyloxy)-2-(3,3,3-trifluoro-2-hydroxy-propyl)-isoindole-1,3-dione

As described for example 8, 4-(4-fluoro-benzyloxy)-phthalic acid (500 mg, 1.7 mmol) was converted to the title compound (567 mg, 86%) [using 3-amino-1,1,1-trifluoro-2-propanol instead of N-acetylethylenediamine] which was obtained as a white solid after purification by chromatography (SiO$_2$, hexane-EtOAc 2:1). MS: m/e=384.3 (M$^+$).

EXAMPLE 43

(5-(4-Fluoro-benzyloxy)-2-(3,3,3-trifluoro-2-methoxy-propyl)-isoindole-1,3-dione To a suspension of sodium hydride (45 mg, 1.0 mmol) in tetrahydrofuran (8 mL) was added 5-(4-fluoro-benzyloxy)-2-(3,3,3-trifluoro-2-hydroxy-propyl)-isoindole-1,3-dione (360 mg, 0.9 mmol) at room temperature and then iodomethane (159 mg, 1.1 mmol) was added and then after 14 h, water was added. The mixture was then extracted with ethylacetate and the combined organic extracts washed with water, brine and then dried over sodium sulfate. Filtration and evaporation gave a residue which was purified by chromatography (SiO$_2$, hexane-EtOAc 3:1) to afford the title compound (120 mg, 32%) as a white solid. MS: m/e=398.4 (M+H$^+$).

EXAMPLE 44

(S)-2-[5-(3-Fluoro-benzyloxy)-1,3-dioxo-1,3-dihydro-isoindol-2-yl]-propionamide a) (S)-2-(5-Hydroxy-1,3-dioxo-1,3-dihydro-isoindol-2-yl)-propionamide As described for example 13a, 4-hydroxyphthalic acid (1.82 g, 1.0 mmol) was converted to the title compound (845 mg, 36%) [using H-Ala-NH$_2$ HCl and pyridine instead of 2-methoxyethylamine] which was obtained as a light yellow solid.

MS: m/e=233.0 (M−H$^−$).

b) (S)-2-[5-(3-Fluoro-benzyloxy)-1,3-dioxo-1,3-dihydro-isoindol-2-yl]-propionamide As described for example 13b, (S)-2-(5-hydroxy-1,3-dioxo-1,3-dihydro-isoindol-2-yl)-propionamide (250 mg, 1.1 mmol) was converted to the title compound (70 mg, 19%) (using 3-fluorobenzylbromide instead of 4-fluorobenzylbromide) which was obtained as a white solid after purification by chromatography (SiO$_2$, CH$_2$Cl$_2$: 2N NH$_3$/MeOH 9:1).

MS: m/e=343.3 (M+H$^+$).

EXAMPLE 45

(2-[5-(3-Fluoro-benzyloxy)-1,3-dioxo-1,3-dihydro-isoindol-2-yl]-acetamide a) 4-(3-Fluoro-benzyloxy)-phthalic acid As described for example 1a and b, 4-hydroxyphthalic acid (5.0 g, 27 mmol) was converted to the title compound (6.9 g, 87%) [using 3-fluorobenzylbromide instead of 4-fluorobenzylbromide) which was obtained as a white solid after recrystallisation from diethyl ether:hexane (1:3). MS: m/e=289.0 (M−H$^−$).

b) (2-[5-(3-Fluoro-benzyloxy)-1,3-dioxo-1,3-dihydro-isoindol-2-yl]-acetamide

As described for example 1d, 4-(3-fluoro-benzyloxy)-phthalic acid (200 mg, 0.69 mmol) was converted to the title compound (151 mg, 66%) which was obtained as a white solid. MS: m/e=328.2 (M$^+$).

EXAMPLE 46

5-(3-Fluoro-benzyloxy)-2-(2-hydroxy-ethyl)-isoindole-1,3-dione

As described for example 8, 4-(3-fluoro-benzyloxy)-phthalic acid (200 mg, 0.69 mmol) was converted to the title compound (179 mg, 82%) [using ethanolamine instead of N-acetylethylenediamine] which was obtained as a white solid after purification by chromatography (SiO$_2$, EtOAc:Hexane 1:1). MS: m/e=315.2 (M$^+$).

EXAMPLE 47

2-(2-Ethylsulfanyl-ethyl)-5-(3-fluoro-benzyloxy)-isoindole-1,3-dione

As described for example 8, 4-(3-fluoro-benzyloxy)-phthalic acid (200 mg, 0.69 mmol) was converted to the title compound (217 mg, 88%) [2-(ethylthio)ethylamine instead of N-acetylethylenediamine] which was obtained as an off-white solid after purification by chromatography (SiO$_2$, EtOAc:Hexane 1:3). MS: m/e=359.2 (M$^+$).

EXAMPLE 48

(5-(3-Fluoro-benzyloxy)-2-(3,3,3-trifluoro-2-hydroxy-propyl)-isoindole-1,3-dione As described for example 8, 4-(3-fluoro-benzyloxy)-phthalic acid (200 mg, 0.69 mmol) was converted to the title compound (235 mg, 89%) [using 3-amino-1,1,1-trifluoro-2-propanol instead of N-acetylethylenediamine] which was obtained as a white solid after purification by chromatography (SiO$_2$, hexane-EtOAc 2:1).

MS: m/e=383.2 (M$^+$).

EXAMPLE 49

5-(3-Fluoro-benzyloxy)-2-(3,3,3-trifluoro-2-methoxy-propyl)-isoindole-1,3-dione

As described for example 43, (5-(3-fluoro-benzyloxy)-2-(3,3,3-trifluoro-2-hydroxy-propyl)-isoindole-1,3-dione (120 mg, 0.31 mmol) was converted to the title compound (25 mg, 21%) which was obtained as a white solid after purification by chromatography (SiO$_2$, hexane-EtOAc 3:1). MS: m/e=398.3 (M+H$^+$).

EXAMPLE 50

2-(2-Amino-ethyl)-5-(3-fluoro-benzyloxy)-isoindole-1,3-dione 1:1 hydrochloride a) {2-[5-(3-Fluoro-benzyloxy)-1,3-dioxo-1,3-dihydro-isoindol-2-yl]-ethyl}-carbamic acid tert-butyl ester As described for example 9a, 4-(3-fluoro-benzyloxy)-phthalic acid (300 mg, 1.0 mmol) was converted to the title compound (338 mg, 79%) which was obtained as a white solid after purification by chromatography (SiO$_2$, hexane-EtOAc 3:1).
MS: m/e=415.4 (M+H$^+$).

b) 2-(2-Amino-ethyl)-5-(3-fluoro-benzyloxy)-isoindole-1,3-dione 1:1 hydrochloride As described for example 9b, {2-[5-(3-fluoro-benzyloxy)-1,3-dioxo-1,3-dihydro-isoindol-2-yl]-ethyl}-carbamic acid tert-butyl ester (311 mg, 0.75 mmol) was converted to the title compound (249 mg, 94%) which was obtained as a white solid.
MS: m/e=315.3 (M+H$^+$).

EXAMPLE 51

[5-(3-Fluoro-benzyloxy)-1,3-dioxo-1,3-dihydro-isoindol-2-yl]-acetonitrile

As described for example 1d, 4-(3-fluoro-benzyloxy)-phthalic acid (200 mg, 0.69 mmol) was converted to the title compound (176 mg, 82%) (using aminoacetonitrile instead of glycinamide hydrochloride) which was obtained as a white solid after purification by chromatography (SiO$_2$, hexane-EtOAc 3:1). MS: m/e=310.2 (M$^+$).

EXAMPLE 52

(S)-2-[5-(3-Fluoro-benzyloxy)-1,3-dioxo-1,3-dihydro-isoindol-2-yl]-3-hydroxy-propionamide

As described for example 8, 4-(3-fluoro-benzyloxy)-phthalic acid (200 mg, 0.69 mmol) was converted to the title compound (76 mg, 31%) [using L-(–)-serinamide HCl and pyridine (65 mg, 0.8 mmol) instead of N-acetylethylenediamine] which was obtained as a light-orange solid. MS: m/e=359.2 (M+H$^+$).

EXAMPLE 53

(S)-5-(3,5-Bis-trifluoromethyl-benzyloxy)-2-(2-methoxy-1-methyl-ethyl)-isoindole-1,3-dione

As described for example 23, a mixture of (S)-5-hydroxy-2-(2-methoxy-1-methyl-ethyl)-isoindole-1,3-dione (200 mg, 0.9 mmol) was converted to title compound (314 mg, 81%) [using 3,5-bis-(trifluoromethyl)benzyl bromide instead of 4-fluorobenzylbromide], after heating under reflux for 1 h, which was obtained as a white solid after crystallization from ethylacetate:hexane (1:1). MS: m/e=461.2 (M$^+$).

EXAMPLE A

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

EXAMPLE D

An injection solution may have the following composition and is manufactured in usual manner:

| Active substance | 1.0 mg |
|---|---|
| 1 N HCl | 20.0 µl |
| acetic acid | 0.5 mg |
| NaCl | 8.0 mg |
| phenol | 10.0 mg |
| 1 N NaOH | q.s. ad pH 5 |
| H$_2$O | q.s. ad 1 ml |

What is claimed is:
1. A method of treating Alzheimer's disease and senile dementia comprising administering to a patient in need of such treatment a therapeutically effective amount of at least one compound of the formula

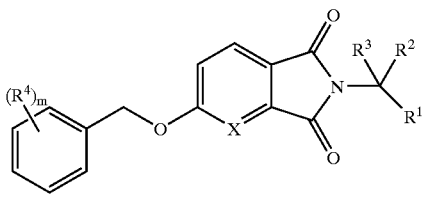

wherein x is —N= or —CH=;

$R^1$ is —CO—$NR^5R^6$;
—$CHR^7$—$(CH_2)_n$—CO—$NR^5R^6$;
—$(CH_2)_n$—$NR^5R^6$;
—$(CH_2)_n$—$COOR^8$;
—$(CH_2)_n$—CN;
—$CHR^7$—$(CH_2)_n$—$CF_3$;
—$(CH_2)_n$—NH—$COR^9$;
—$(CH_2)_n$—NH—$COOR^8$;

a heterocyclic ring group selected from —$(CH_2)_n$-piperidinyl,
—$(CH_2)_n$-morpholinyl, —$(CH_2)_n$-tetrahydrofuranyl;
—$(CH_2)_n$-thiophenyl or —$(CH_2)_n$-isoxazolyl, wherein the heterocyclic ring may be substituted by $C_1$–$C_6$-alkyl;

a phenyl;
—$(CH_2)_n$-phenyl, wherein the phenyl ring may be substituted by halogen or halogen-($C_1$–$C_6$)-alkyl;
—$(CH_2)_p$—$OR^8$;
—$(CH_2)_p$—$SR^8$;
—$(CH_2)_p$—SO—$R^9$; or
—$(CH_2)_n$—CS—$NR^5R^6$;

$R^2$ is hydrogen;
$C_1$–$C_6$-alkyl;
—$(CH_2)_p$—$OR^{10}$;
—$(CH_2)_p$—$SR^{10}$; or benzyl;

$R^3$ is hydrogen or $C_1$–$C_6$-alkyl;

$R^4$ is halogen, halogen-($C_1$–$C_6$)-alkyl, cyano, $C_1$–$C_6$-alkoxy or halogen-($C_1$–$C_6$)-alkoxy;

$R^5$ and $R^6$ are independently from each other hydrogen or $C_1$–$C_6$-alkyl;

$R^7$ is hydrogen, hydroxy or $C_1$–$C_6$-alkoxy;

$R^8$ is hydrogen or $C_1$–$C_6$-alkyl;

$R^9$ is $C_1$–$C_6$-alkyl;

$R^{10}$ is hydrogen or $C_1$–$C_6$-alkyl;

m is 1, 2 or 3;

n is 0, 1 or 2; and p is 1 or 2;

or a pharmaceutically acceptable salt thereof.

2. A process for the manufacture of a compound of formula I

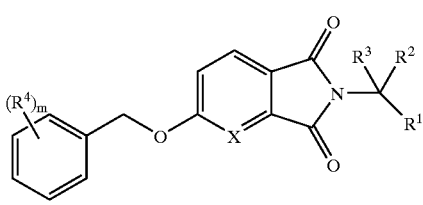

wherein

X is —N= or —CH=;

$R^1$ is —CO—$NR^5R^6$;
—$CHR^7$—$(CH_2)_n$—CO—$NR^5R^6$;
—$(CH_2)_n$—$NR^5R^6$;
—$(CH_2)_n$—$COOR^8$;
—$(CH_2)_n$—CN;
—$CHR^7$—$(CH_2)_n$—$CF_3$;
—$(CH_2)_n$—NH—$COR^9$;
—$(CH_2)_n$—NH—$COOR^8$;

a heterocyclic ring group selected from —$(CH_2)_n$-piperidinyl,
—$(CH_2)_n$-morpholinyl, —$(CH_2)_n$-tetrahydrofuranyl;
—$(CH_2)_n$-thiophenyl or —$(CH_2)_n$-isoxazolyl, wherein the heterocyclic ring may be substituted by $C_1$–$C_6$-alkyl;

a phenyl;
—$(CH_2)_n$-phenyl, wherein the phenyl ring may be substituted by halogen or halogen-($C_1$–$C_6$)-alkyl;
—$(CH_2)_p$—$OR^8$;
—$(CH_2)_p$—$SR^8$;
—$(CH_2)_p$—SO—$R^9$; or
—$(CH_2)_n$—CS—$NR^5R^6$;

$R^2$ is hydrogen;
$C_1$–$C_6$-alkyl;
—$(CH_2)_p$—$OR^{10}$;
—$(CH_2)_p$—$SR^{10}$; or benzyl;

$R^3$ is hydrogen or $C_1$–$C_6$-alkyl;

$R^4$ is halogen, halogen-($C_1$–$C_6$)-alkyl, cyano, $C_1$–$C_6$-alkoxy or halogen-($C_1$–$C_6$)-alkoxy;

$R^5$ and $R^6$ are independently from each other hydrogen or $C_1$–$C_6$-alkyl;

$R^7$ is hydrogen, hydroxy or $C_1$–$C_6$-alkoxy;

$R^8$ is hydrogen or $C_1$–$C_6$-alkyl;

$R^9$ is $C_1$–$C_6$-alkyl;

$R^{10}$ is hydrogen or $C_1$–$C_6$-alkyl;

m is 1, 2 or 3;

n is 0, 1 or 2; and p is 1 or 2;

which process comprises a) reacting a compound of formula

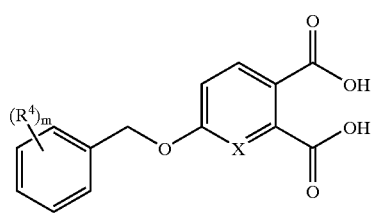

with a compound of formula

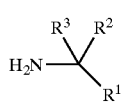

to obtain a compound of formula I.

3. A process for the manufacture of a compound of formula I

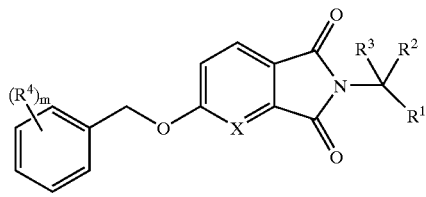

wherein
X is —N= or —CH=;
R$^1$ is —CO—NR$^5$R$^6$;
—CHR$^7$—(CH$_2$)$_n$—CO—NR$^5$R$^6$;
—(CH$_2$)$_n$—NR$^5$R$^6$;
—(CH$_2$)$_n$—COOR$^8$;
—(CH$_2$)$_n$—CN;
—CHR$^7$—(CH$_2$)$_n$—CF$_3$;
—(CH$_2$)$_n$—NH—COR$^9$;
—(CH$_2$)$_n$—NH—COOR$^8$;
a heterocyclic ring group selected from —(CH$_2$)$_n$-piperidinyl,
—(CH$_2$)$_n$-morpholinyl, —(CH$_2$)$_n$-tetrahydrofuranyl;
—(CH$_2$)$_n$-thiophenyl or —(CH$_2$)$_n$-isoxazolyl, wherein the heterocyclic ring may be substituted by C$_1$–C$_6$-alkyl;
a phenyl;
—(CH$_2$)$_n$-phenyl, wherein the phenyl ring may be substituted by halogen or halogen-(C$_1$–C$_6$)-alkyl;
—(CH$_2$)$_p$—OR$^8$;
—(CH$_2$)$_p$—SR$^8$;
—(CH$_2$)$_p$—SO—R$^9$; or
—(CH$_2$)$_p$—CS—NR$^5$R$^6$;
R$^2$ is hydrogen;
C$_1$–C$_6$-alkyl;
—(CH$_2$)$_p$—OR$^{10}$;
—(CH$_2$)$_p$—SR$^{10}$; or benzyl;
R$^3$ is hydrogen or C$_1$–C$_6$-alkyl;
R$^4$ is halogen, halogen-(C$_1$–C$_6$)-alkyl, cyano, C$_1$–C$_6$-alkoxy or halogen-(C$_1$–C$_6$)-alkoxy;
R$^5$ and R$^6$ are independently from each other hydrogen or C$_1$–C$_6$-alkyl;
R$^7$ is hydrogen, hydroxy or C$_1$–C$_6$-alkoxy;
R$^8$ is hydrogen or C$_1$–C$_6$-alkyl;
R$^9$ is C$_1$–C$_6$-alkyl;
R$^{10}$ is hydrogen or C$_1$–C$_6$-alkyl;
m is 1, 2 or 3;
n is 0, 1 or 2; and
p is 1 or 2;
which process comprises reacting a compound of formula

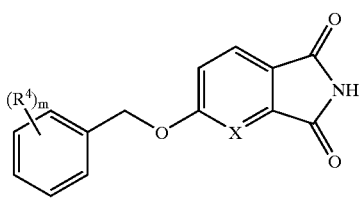

with a compound of formula

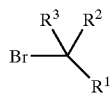

to obtain a compound of formula I.

* * * * *

UNITED STATES PATENT AND TRADEMARK OFFICE
CERTIFICATE OF CORRECTION

PATENT NO.     : 6,903,095 B2
DATED          : June 7, 2005
INVENTOR(S)    : Cesura et al.

It is certified that error appears in the above-identified patent and that said Letters Patent is hereby corrected as shown below:

Title page,
Item [74], *Attorney, Agent, or Firm*, reads "George W. Johnston; Patricia S. Roca-Tramaloni; Kimberly J. Prior" should read -- George W. Johnston; Patricia S. Rocha-Tramaloni; Kimberly J. Prior --.

Signed and Sealed this

Fourth Day of October, 2005

JON W. DUDAS
*Director of the United States Patent and Trademark Office*